United States Patent [19]
Rozell

[11] Patent Number: 6,106,493
[45] Date of Patent: Aug. 22, 2000

[54] SHOULDER STABILIZER

[76] Inventor: Michael David Rozell, 7216 Santa Fe Dr., Overland Park, Kans. 66204

[21] Appl. No.: 08/811,822
[22] Filed: Mar. 4, 1997
[51] Int. Cl.$^7$ .......................................................... A61F 5/00
[52] U.S. Cl. .................................... 602/20; 602/4; 602/5; 602/62; 128/874; 2/45
[58] Field of Search .............................. 602/4, 5, 20, 21; 2/456, 459, 44, 45

[56] References Cited

U.S. PATENT DOCUMENTS

| | | |
|---|---|---|
| 4,716,895 | 1/1988 | Marques et al. ............................. 602/4 |
| 5,358,470 | 10/1994 | Johnson ................................... 602/4 X |
| 5,403,268 | 4/1995 | Clement .................................. 602/4 X |
| 5,609,569 | 3/1997 | Offenhartz ............................. 602/20 X |
| 5,628,725 | 5/1997 | Ostergard ............................... 602/20 X |

Primary Examiner—Kim M. Lee
Attorney, Agent, or Firm—Litman, Kraai & Brown L.L.C.

[57] ABSTRACT

A brace for supporting a wearer's shoulder joint during movement is made of elastic material and comprises a torso strap, a shoulder strap, upper and lower stabilizing straps and a vertical support strap. The torso strap is securable around the torso of the wearer generally across the lower end of the rib cage. The shoulder strap is secured at a first end to the torso strap on a side opposite the shoulder to be supported. The shoulder strap extends across the front of the wearer, over and around the shoulder to be supported and across the back of the wearer and is removably securable at a second end to the torso strap along the side opposite the supported shoulder. The shoulder strap is secured to the torso strap under tension to provide the desired support to the shoulder. The upper and lower stabilizing straps cooperate with the shoulder strap to form a shoulder receiving pocket in the shoulder strap and help hold the shoulder strap in place. Similarly the vertical support strap helps hold the shoulder strap in place during use.

14 Claims, 2 Drawing Sheets

SHOULDER STABILIZER

BACKGROUND OF THE INVENTION

1. Field of the Invention.

The present invention relates to orthopedic braces for supporting the shoulder

2. Prior Art.

The shoulder joint is an inherently unstable joint due to the relatively large convex humeral head which seats in the significantly smaller concave glenoid fossa or socket. Due to this instability, the humeral head is prone to excessive anterior and/or superior translation relative to the glenoid fossa. The muscles, ligaments and tendons surrounding the shoulder joint do provide a degree of stability. However, because of its construction, the shoulder joint is prone to injury. In particular, chronic stress from repetitive instances of excess anterior and/or superior translation of the humeral head can cause irreversible damage to the tensile strength of the tissues which provide anterior and superior restraint of the humeral head within the socket.

Once an injury to the shoulder joint occurs, it may be necessary to support the joint while the underlying injury or pathology is being corrected such as through rehabilitation. Further, for those who have permanently weakened their shoulder joint through previous injuries, it is helpful to provide dynamic support for the shoulder joint to increase performance of the shoulder joint while reducing the risk of further injury. Although various shoulder braces have been developed to provide dynamic support of the shoulder, existing braces tend to be fairly complicated, expensive and difficult for the wearer to don by themselves.

SUMMARY OF THE INVENTION

The present invention comprises a brace for supporting a wearer's shoulder joint during movement. The brace is of one piece construction and preferably formed from a stretchable material. The brace comprises a torso strap, a shoulder strap, upper and lower stabilizing straps and a vertical restraining strap.

The torso strap has opposed ends which are securable together to form a loop such that the torso strap may be secured around the torso of the wearer generally across the lower end of the rib cage. The shoulder strap is secured at a first end to the torso strap and a second or free end of the shoulder strap has a fastener secured thereto. The shoulder strap generally extends away from the torso strap at an acute angle thereto and is wrapped back over itself to form a shoulder receiving pocket. The shoulder strap then extends back toward the torso strap at an acute angle thereto.

The fastener on the second end of said shoulder strap is removably securable to the torso strap proximate the first end of the shoulder strap. When the brace is put on the shoulder to be supported is positioned in the shoulder receiving pocket and the free end of shoulder strap is pulled taut and fastened to the torso belt such that the shoulder strap pulls rearwardly and downwardly on the shoulder joint to resist anterior and superior displacement of the humeral head relative to the socket.

The upper stabilizing strap generally extends between front and rear portions of the shoulder strap along an upper edge thereof and on opposite sides of said shoulder receiving pocket. When the brace is donned, the upper stabilizing strap generally extends over and across the wearer's trapezius muscle and operates to keep the shoulder strap in proper alignment over the shoulder and to keep the shoulder strap from sliding downwardly off of the shoulder.

The lower stabilizing strap extends between front and rear portions of the shoulder strap along a lower edge thereof and on opposite sides of the shoulder receiving pocket so as to form an arm receiving opening between it and a lower edge of the shoulder strap. When putting the brace on, the wearer inserts their arm through the arm receiving opening such that the lower stabilizing strap extends below the wearer's arm. The lower stabilizing strap helps maintain the shoulder strap in the proper position and operates to prevent the shoulder strap from sliding upwards along the wearer's trapezius muscle when the wearer raises their arm.

The vertical support strap is secured to and extends between the torso strap and the rear portion of the shoulder strap along the lower edge thereof and proximate the arm receiving opening. The vertical support strap helps in preventing the shoulder strap from turning upward along its outer or lower edge and from sliding up along the wearer's trapezium muscle. The vertical support strap also provides resistance to superior translation of the shoulder joint.

Objects and Advantages of the Invention

Therefor the objects of the present invention include; to provide a shoulder brace which restrains the humeral head from anterior and superior displacement; to provide such a brace which supports the shoulder joint during movement of the arm; to provide such a brace having a shoulder strap which extends over and across the shoulder joint under tension; to provide such a brace which may be donned without assistance; to provide such a brace in which the tension on the shoulder strap is adjustable; to provide such a brace which is of one piece construction; to provide such a brace which is relatively lightweight; to provide such a brace which is relatively inexpensive; and to provide such a brace which is particularly well adapted for its intended purpose thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 5:
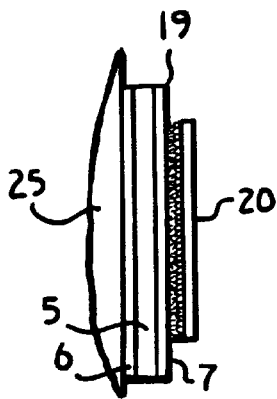
FIG. 5 is an enlarged and fragmentary cross-sectional view taken generally along line 5—5 of FIG. 4 in which the dimensions have been distorted to show the layers of the material forming the shoulder brace.

Referring to the drawings in more detail, the reference numeral 1 refers to a shoulder brace of the present invention adapted for use in supporting a shoulder 2 of a wearer 3. The brace 1 is preferably constructed of a composite of Neoprene synthetic rubber 5 sandwiched between an inner and an outer layer of fabric 6 and 7 respectively such as the material sold under the name UBL/Neoprene as generally shown in FIG. 5. The outer layer of fabric 7 has a weave which allows the outer surface of the outer layer of fabric 7 to generally function as a loop portion of a hook and loop type fastener, such that when a hook portion of a hook and loop type fastener is pressed against the outer layer of fabric 7, the hook portion adheres thereto.

The brace 1 comprises a torso or waist strap 10, a shoulder strap 11, an upper stabilizing strap 12, a lower stabilizing strap 13 and a vertical support strap 14. The torso strap 10 has first and second ends 18 and 19, one of which (end 18 in the embodiment shown) has a first hook portion 20 of a hook and loop type fastener secured thereto. The torso strap is sized for wrapping around the torso of a wearer, generally across the lower portion of the rib cage of the wearer 3, with the first and second ends 18 and 19 securable together in overlapping relationship with the first hook portion 20 on end 18 engaging the outer layer of fabric 7 of end 19 for securing the ends 18 and 19 together. The degree to which ends 18 and 19 overlap and are secured together is thereby adjustable to accommodate wearer's of differing girths. The brace 1 is preferably configured such that the ends 18 and 19 are securable together proximate a first side 21 of the wearer 3, corresponding to the side of the shoulder 2 to be supported and generally toward the front thereof.

The shoulder strap 11 includes a first end 22 and a second end 23. In the preferred embodiment, the first end 22 of the shoulder strap 11 is integrally formed with the torso strap 10. The first end 22 of the shoulder strap 11 extends from or is secured to the torso strap 10 generally medially thereof and at an acute angle relative to the portion of the torso strap 10 which is adapted to extend across the front of the wearer 3. When the brace 1 is donned the first end 22 of the shoulder strap 11 is secured to the torso strap generally along a second side 25 of the wearer, the side opposite the shoulder 2 to be supported and generally toward the front thereof.

The shoulder strap 11 extends upward and away from the torso strap 10 at an acute angle and then is wrapped or curved around approximately 180 degrees so as to extend back toward the torso strap 10 such that the shoulder strap 11 includes a front portion 27 a back portion 28 and a shoulder receiving pocket 29. The shoulder strap 11 also includes a lower or outer edge 30 and an upper or inner edge 31. Two second hook portions 35 of a hook and loop type fastener are secured to the shoulder strap 11 at the second end 23 thereof for use in securing the shoulder strap second end 23 to the torso belt 10 generally along the second side 25 of the wearer 3.

The upper and lower stabilizing straps 12 and 13 are generally arcuate and are secured to the shoulder strap 11 on opposite sides thereof. Front and rear ends 40 and 41 of the upper stabilizing strap 12 are secured to and extend between the front and back portions 27 and 28 respectively of the shoulder strap 11 along the upper edge 31 thereof and on opposite sides of the shoulder receiving pocket 29. Front and rear ends 42 ad 43 of the lower stabilizing strap 13 are secured to and extend between the front and back portions 27 and 28 of the shoulder strap 11 along the lower edge 30 thereof and on opposite sides of the shoulder receiving pocket 29. The lower stabilizing strap 13 forms an arm receiving opening 46 between it and the lower edge 30 of the shoulder strap 11 adjacent the shoulder receiving pocket 29.

Figure 1:
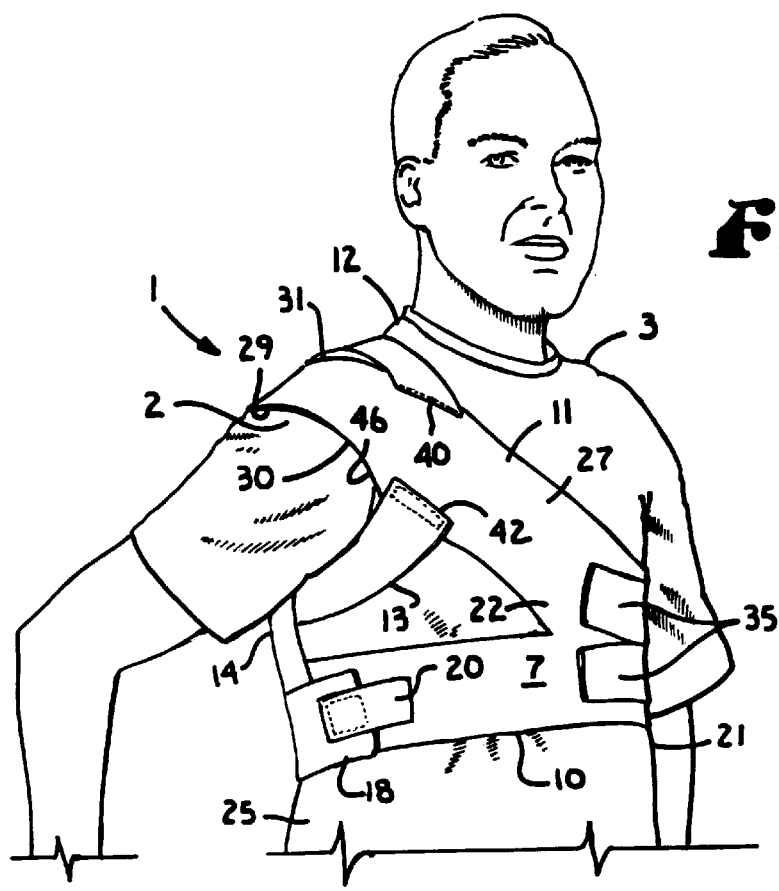
FIG. 1 is a front, left side perspective view showing a shoulder brace of the present invention secured in position for supporting a shoulder of a wearer.
Figure 2:
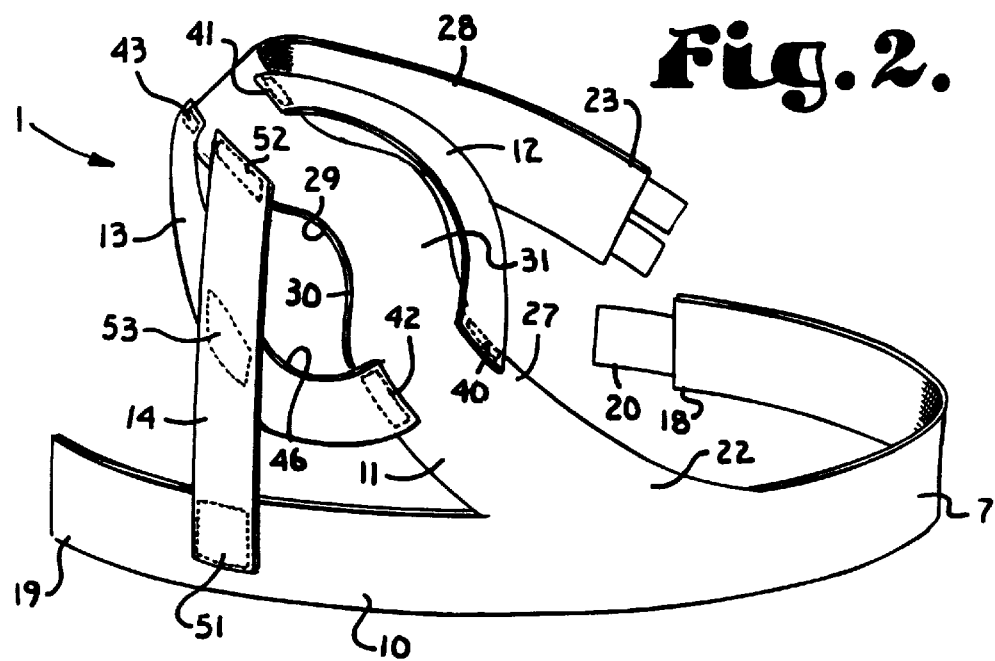
FIG. 2 is an enlarged view of the shoulder brace as shown in FIG. 1 removed from the wearer.
Figure 3:
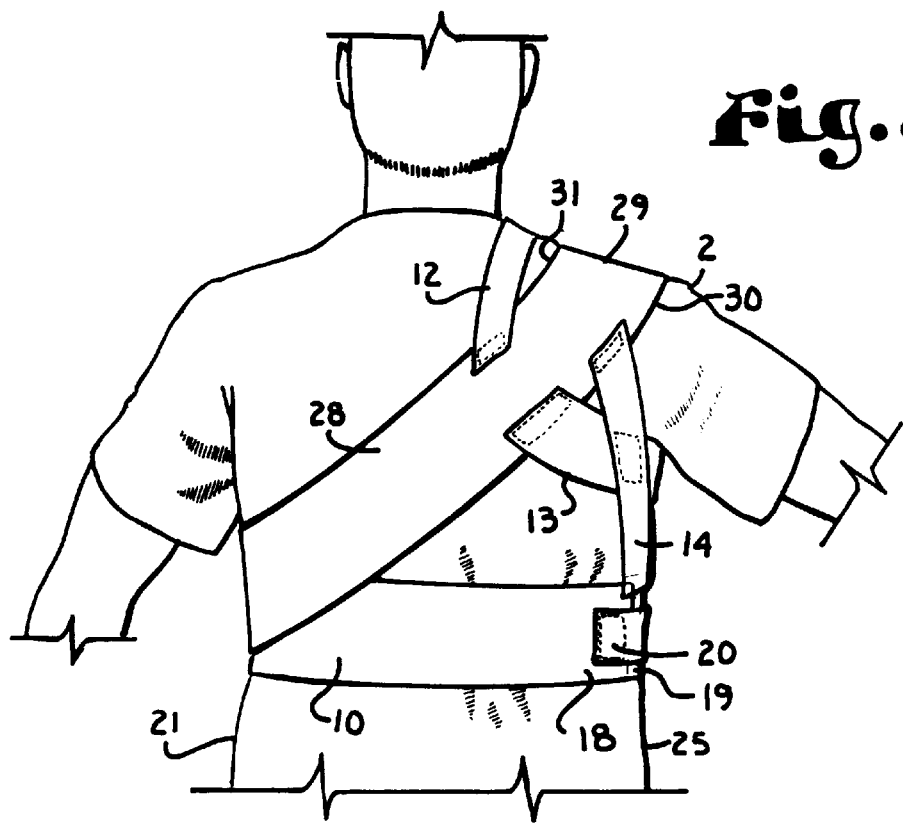
FIG. 3 is a rear elevational view of the shoulder brace secured to a wearer as in FIG. 1.
Figure 4:
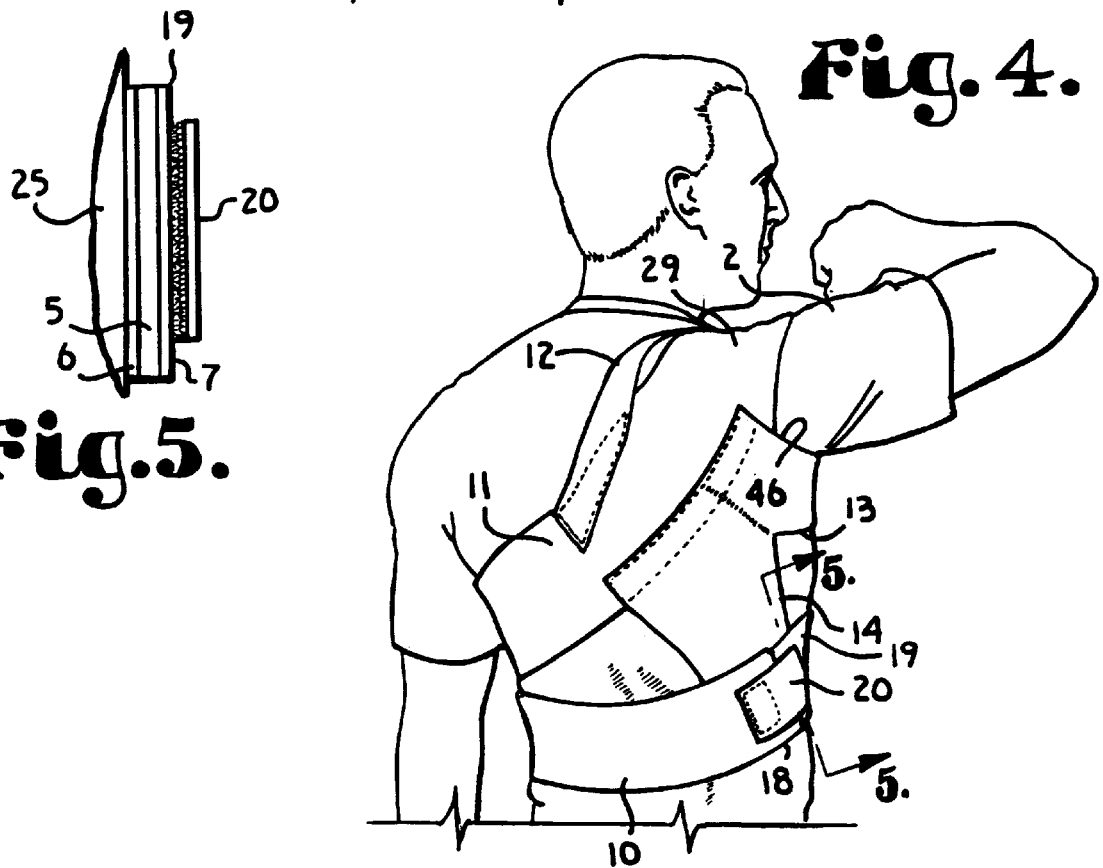
FIG. 4 is rear right side perspective view showing an alternative embodiment of the shoulder brace of the present invention secured in position for supporting a shoulder of a wearer.

The vertical support strap 14 is secured at a first end 51 to the torso strap 10 and at a second end 52 to the shoulder strap 11 along a lower edge thereof and proximate the rear end 43 of the lower stabilizing strap 13. In the embodiment as shown in FIGS. 1 through 3, the second end 52 of the vertical support strap 14 is secured to the shoulder strap 11 slightly in front of the rear end 43 of the lower stabilizing strap 13. The vertical support strap 14 is also secured to the lower stabilizing strap 13 at a point of intersection 53. It is foreseen that the vertical support strap 14 could be integrally formed with the lower stabilizing strap 13 as generally shown in FIG. 4.

The brace 1 is secured in place by inserting the arm, associated with the shoulder 2 to be supported, through the arm receiving opening 46 such that the lower stabilizing strap 13 extends just below the arm generally across the armpit, the upper stabilizing strap 12 generally extends over and across the wearer's trapezius muscle, and the shoulder 2 is generally positioned in the shoulder receiving pocket 29. The torso strap 10 is then wrapped around the wearer's torso, generally across the lower portion of the wearer's rib cage, such that first end 18 overlaps the second end 19. The ends 18 and 19 are pulled together in overlapping relation to provide a snug fit around the torso and then the first hook portion 20 is pressed against the outer layer of fabric 7 of the torso strap 10 to secure the torso strap 10 in place.

The wearer then grasps the second end 23 of the shoulder strap 11 and pulls the shoulder strap second end 23 across the back and generally around the wearer's second side 25 such that the shoulder strap 11 is under tension. The second hook portion 35 on the shoulder strap 11 second end 23 is then pressed against the outer layer of fabric 7 of the torso strap 10 to secure the shoulder strap second end 23 in place with the shoulder strap 11 under tension.

The tension in the shoulder strap 11 exerts a downwardly and rearwardly directed force on the humeral head of the shoulder to be supported so as to resist anterior or superior displacement from the socket. The elasticity of the brace 1, allows the arm associated with the supported shoulder 2, to move through the full range of motions while providing support for the shoulder 2. The shoulder strap 11 also assists with deceleration of the upper extremity such as during a throwing motion.

Various features of the brace 1 cooperate to hold the shoulder strap 11 in place. The fabric inner surface of the brace 1 resists slipping of the components of the brace including the shoulder strap 11. The upper stabilizing strap 12 helps hold the shoulder strap 11 in place and generally restrains the shoulder strap 11 from sliding off the shoulder 2 and down the arm. The lower stabilizing strap 13 restrains the shoulder strap 11 from sliding upward off the shoulder 2 generally along the trapezius such as when the arm is raised. The lower stabilizing strap 13 also restrains the lower edge 30 of the shoulder strap 11 from rolling up as the arm is raised. The vertical support strap 14 similarly restrains the shoulder strap 11 from sliding or rolling upward off the shoulder 2 and provides additional resistance to raising of the arm which helps in maintaining the humeral head properly aligned and seated relative to the socket when the arm is raised.

FIG. 4 shows an alternative embodiment of the brace of the present invention comprising the same components except that the vertical support strap 14 extends between the shoulder strap 11 and the torso strap 10 behind the lower stabilizing strap 13. An upper portion of the vertical support strap 14 is connected to or integrally formed with a rear portion of the lower stabilizing strap 13. The vertical support strap 14 generally connects the torso strap 10 to the shoulder strap 11. It is foreseen that the vertical support strap 14 could only extend between the torso strap 10 and the lower stabilizing strap 13 in which case the vertical support strap 14 should still be deemed to connect the torso strap 10 to the shoulder strap 11 although the connection is indirect.

It is to be understood that while certain forms of the present invention have been illustrated and described herein, it is not to be limited to the specific forms or arrangement of parts described and shown.

What is claimed and desired to be secured by Letters Patent is as follows:

1. A brace for supporting a wearer's shoulder joint comprising:
   (a) a torso strap securable around the torso of the wearer;
   (b) a shoulder strap secured at a first end to said torso strap on a first side of the wearer opposite the shoulder to be supported and extending at an acute angle across the front of the wearer, over the shoulder to be supported and across the back of the wearer and back toward the torso strap on the first side of the wearer; said shoulder strap having a fastener secured to a second end thereof for securing said second end of said shoulder strap to said torso strap along the first side of the wearer;
   (c) an upper stabilizing strap fixedly secured at opposite ends to a front portion and a back portion of said shoulder strap along an upper edge thereof so as to generally extend across the wearer's trapezius muscle adjacent the shoulder joint to be stabilized; and
   (d) a lower stabilizing strap fixedly secured at opposite ends to a front portion and a back portion of said shoulder strap along a lower edge thereof so as to generally extend under the arm of the shoulder joint to be stabilized; said lower stabilizing strap forming an arm receiving opening with said shoulder strap for extension of the wearer's arm therethrough.

2. The brace as in claim 1 further comprising:
   (a) a vertical support strap fixedly secured to and extending between said torso strap and said back portion of said shoulder strap along said lower edge thereof and proximate said arm receiving opening.

3. The brace as in claim 1 further comprising:
   (a) a vertical support strap fixedly connecting said torso strap to said shoulder strap proximate said shoulder receiving pocket.

4. The brace as in claim 1 wherein:
   (a) said brace is formed from an elastic material having an outer surface which functions as a loop portion of a hook and loop type fastener; and
   (b) said fastener secured to said second end of said shoulder strap comprises a first hook portion of a hook and loop type fastener.

5. The brace as in claim 1 wherein:
   (a) said torso strap includes opposed ends one of which has a second hook portion of a hook and loop type fastener secured thereto for securing said opposed ends together in overlapping relationship.

6. A brace for supporting a wearer's shoulder joint comprising:
   (a) a torso strap having first and second ends and a first hook portion of a hook and loop type fastener secured to said torso strap first end;
   (b) a shoulder strap having a first end connected to said torso strap and a second end having a second hook portion of a hook and loop type fastener secured thereto; said shoulder strap extending from said torso strap at an angle thereto and wrapped back over itself to form a shoulder receiving pocket and extending back toward said torso strap at an angle thereto;
   (c) an upper stabilizing strap secured to and extending between front and rear portions of said shoulder strap along an upper edge thereof and on opposite sides of said shoulder receiving pocket;
   (d) a lower stabilizing strap secured to and extending between said front and rear portions of said shoulder strap along a lower edge thereof and on opposite sides of said shoulder receiving pocket; said lower stabilizing strap forming an arm receiving opening between said lower stabilizing strap and said shoulder strap;
   (e) a vertical support strap connecting said torso strap to said shoulder strap proximate said shoulder receiving pocket; and
   (f) wherein said torso strap, said shoulder strap; said upper stabilizing strap; said lower stabilizing strap and said vertical support strap are formed from an elastic material having an outer surface which functions as a loop portion of a hook and loop type fastener.

7. A brace for supporting a wearer's shoulder joint comprising:
   (a) a torso strap;
   (b) a shoulder strap having a first end connected to said torso strap and a second end having a fastener secured thereto; said shoulder strap extending from said torso strap at an angle thereto and wrapped back over itself to form a shoulder receiving pocket and extending back toward said torso strap at an angle thereto; said fastener on said second end of said shoulder strap being removably securable to said torso strap;
   (c) at least a lower stabilizing strap fixedly secured to and extending between said front and rear portions of said shoulder strap along a lower edge thereof and on opposite sides of said shoulder receiving pocket; said lower stabilizing strap forming an arm receiving opening between said lower stabilizing strap and said shoulder strap; and
   (d) a vertical support strap fixedly secured to and extending between said torso strap and said rear portion of said shoulder strap along said lower edge thereof and proximate said arm receiving opening.

8. The brace as in claim 7 further comprising:
   (a) an upper stabilizing strap fixedly secured to and extending between front and rear portions of said shoulder strap along an upper edge thereof and on opposite sides of said shoulder receiving pocket.

9. The brace as in claim 7 wherein:
   (a) said brace is formed from an elastic material having an outer surface which functions as a loop portion of a hook and loop type fastener; and
   (b) said fastener secured to said second end of said shoulder strap comprises a first hook portion of a hook and loop type fastener.

10. The brace as in claim 9 wherein:
(a) one of said opposed ends of said torso strap has a second hook portion of a hook and loop type fastener secured thereto.

11. A brace for supporting a wearer's shoulder joint comprising:
(a) a torso strap;
(b) a shoulder strap having a first end connected to said torso strap and a second end having a fastener secured thereto; said shoulder strap extending from said torso strap at an angle thereto and wrapped back over itself to form a shoulder receiving pocket and extending back toward said torso strap at an angle thereto; said fastener on said second end of said shoulder strap being removably securable to said torso strap;
(c) at least a lower stabilizing strap fixedly secured to and extending between said front and rear portions of said shoulder strap along a lower edge thereof and on opposite sides of said shoulder receiving pocket; said lower stabilizing strap forming an arm receiving opening between said lower stabilizing strap and said shoulder strap; and
(d) a vertical support strap fixedly secured to and extending between said torso strap and said lower stabilizing strap.

12. The brace as in claim 11 further comprising:
(a) an upper stabilizing strap fixedly secured to and extending between front and rear portions of said shoulder strap along an upper edge thereof and on opposite sides of said shoulder receiving pocket.

13. The brace as in claim 11 wherein:
(a) said brace is formed from an elastic material having an outer surface which functions as a loop portion of a hook and loop type fastener; and
(b) said fastener secured to said second end of said shoulder strap comprises a first hook portion of a hook and loop type fastener.

14. The brace as in claim 13 wherein:
(a) one of said opposed ends of said torso strap has a second hook portion of a hook and loop type fastener secured thereto.

* * * * *